United States Patent [19]
Spencer

[11] Patent Number: 5,993,207
[45] Date of Patent: Nov. 30, 1999

[54] ORTHODONTIC ACCESSORY FOR CORRECTIVE FORCE APPLICATION TO ORTHODONTIC BRACKET

[76] Inventor: William A. Spencer, 8800 Kings Lynn La., Louisville, Ky. 40220

[21] Appl. No.: 09/167,615

[22] Filed: Oct. 6, 1998

[51] Int. Cl.$^6$ ........................................................ A61L 3/00
[52] U.S. Cl. .................................................. 433/18; 433/8
[58] Field of Search ................................. 433/21, 14, 16, 433/18, 13, 8, 22

[56] References Cited

U.S. PATENT DOCUMENTS

| | | | |
|---|---|---|---|
| 3,262,207 | 7/1966 | Kesling | 433/21 |
| 4,242,085 | 12/1980 | Wallshein | 433/14 |
| 4,350,487 | 9/1982 | Kesling et al. | 433/14 |
| 4,664,626 | 5/1987 | Kesling | 433/16 |
| 4,676,747 | 6/1987 | Kesling | 433/18 |
| 4,799,882 | 1/1989 | Kesling | 433/8 |
| 4,975,052 | 12/1990 | Spencer et al. | 433/21 |
| 5,160,261 | 11/1992 | Peterson | 433/8 |
| 5,470,228 | 11/1995 | Franseen et al. | 433/8 |

FOREIGN PATENT DOCUMENTS

| | | | |
|---|---|---|---|
| WO 97/14370 | 4/1997 | WIPO | 433/14 |

OTHER PUBLICATIONS

"Auxiliary Springs in Continuous Arch Treatment: Part 2. Appliance Use and Case Reports", Haskell, et al., American Journal of Orthodontic Dentofac. Orthop., vol. 98, No. 6, pp. 488–498, Dec. 1990.

"Serving Orthodontics Around the World", TP Orthodontics, Inc. Product Catalog, pp. 6, 17,44, 115–135.

*Primary Examiner*—John J. Wilson
*Assistant Examiner*—Patrick A. Hilsmier
*Attorney, Agent, or Firm*—Holme Roberts & Owen LLP

[57] ABSTRACT

An improved orthodontic accessory for transmitting corrective forces from a corrective force generation device to an orthodontic bracket securable on a tooth generally includes a pin interconnected at one end with a channel defining member. The pin is insertable in a pin receiving slot of an orthodontic bracket also having a primary arch wire slot for receiving an arch wire therethrough. The bracket may be an Edgewise orthodontic bracket and the pin receiving slot may extend vertically. The channel defining member defines a channel, which extends laterally in at least one of a mesial and a distal direction and which may be closed, for receiving a corrective force generation device therethrough. Corrective forces applied by the corrective force generation device to the channel defining member are transmittable to the orthodontic bracket by the pin. A method of applying corrective forces to a patient's tooth involves attaching an orthodontic bracket to the tooth, inserting the pin of the disclosed orthodontic accessory device into a vertically extending slot of the bracket, and engaging a corrective force generation device in the channel of the accessory device. A portion of the pin may be bent to secure the accessory device to the bracket, and, after the corrective forces are applied to the tooth for a period of time, the corrective force generation device may be disengaged from the channel and the pin may be removed from the vertically extending slot to remove the accessory device from the bracket.

42 Claims, 5 Drawing Sheets

ORTHODONTIC ACCESSORY FOR CORRECTIVE FORCE APPLICATION TO ORTHODONTIC BRACKET

FIELD OF THE INVENTION

The present invention generally relates to orthodontic appliances and, more particularly, relates to an accessory device and associated method for the application of corrective forces to a patient's tooth.

BACKGROUND OF THE INVENTION

Traditionally orthodontic treatment involves the application of corrective forces to one or more of a patient's teeth in order to move and properly align the teeth. Orthodontic brackets secured on the teeth are often used to transmit corrective forces generated by other orthodontic auxiliary devices to the teeth. The corrective forces may be generated by corrective force generation devices, such as springs, wires, hooks, rubber bands, torquing auxiliaries, cuspid retraction devices and the like.

Brackets known in the art are typically classified as an Edgewise type bracket or a Lightwire type bracket. Edgewise brackets are characterized by their relatively wide mesial-distal extent and a labially opening, horizontal slot defined between one or more pair of opposing tie wings for receiving an arch wire therethrough. The arch wire is often retained in the slot by a steel or elastomeric ligating device. Lightwire brackets are characterized by their relatively narrow mesial-distal extent and a vertical slot for receiving a pin used to retain an arch wire in an occlusal facing opening of the Lightwire bracket. Often the Lightwire pins include auxiliary means for dynamically acting between the Lightwire bracket and the arch wire.

As modern orthodontic techniques have evolved, Edgewise brackets having Lightwire type vertical slots have become available. Relatedly, special cuspid brackets adapted for use with cuspid retractor devices exist. Known cuspid retractor brackets often include a labially opening, horizontal slot for receiving an arch wire therethrough and a another horizontal, integral gingival auxiliary tube for receiving a cuspid retraction device mesial-distally therethrough.

To apply appropriate corrective forces to a patient's tooth, a practitioner typically mounts an appropriate bracket on the tooth, secures an arch wire in the arch wire slot (e.g., with a ligature), and if necessary, employs another suitable corrective force generation device. For example, when a practitioner wishes to move a cuspid distally, the practitioner may secure a special cuspid bracket on the cuspid and employ a special cuspid retraction device that engages the horizontal, integral gingival auxiliary tube of the cuspid bracket.

Sometimes, in order to achieve different treatment objectives, different suitable corrective force generation devices must be installed in the auxiliary slot of a bracket at different times during the treatment period. Furthermore, at certain times during the treatment period, only the arch wire may be required and additional corrective force generation devices may be removed.

SUMMARY OF THE INVENTION

It is an object of the present invention to provide a device and method whereby corrective forces generated by a corrective force generation device are transmittable to an orthodontic bracket securable on a tooth and thereby to the tooth itself and the supporting bone structure.

A further object of the present invention is to provide an enhanced arrangement for applying forces to a tooth, including enhanced torquing forces and/or angulating forces.

Another object of the present invention is to provide for the transmission of corrective forces from the corrective force generation device to the orthodontic bracket without displacement of a main arch wire secured in a primary arch wire slot of the orthodontic bracket.

Yet another object of the present invention is to provide for engagement of a corrective force generation device with a relatively small profile orthodontic bracket not having a horizontal, integral gingival auxiliary tube.

These and other objectives and advantages are achieved by various aspects of the present invention. According to one aspect of the present invention, an orthodontic accessory device includes a pin interconnected at one end with a channel defining member. The pin is adapted for use with an orthodontic bracket having a primary slot for receiving an arch wire and a pin receiving slot. More particularly, the pin is sized for insertion into the pin receiving slot. As will be appreciated, the pin receiving slot may be referred to in the orthodontic industry as a vertical slot. In the context of the present invention, the pin receiving slot may assume a range of angles relative to an occlusal plane.

The channel defining member defines a channel that extends laterally relative to the peripheral outer surface of the pin in a mesial and/or distal direction. In this regard, the channel preferably extends mesially and/or distally beyond the peripheral outer pin surface by at least about 0.02 inches, and most preferably by between about 0.04 inches and 0.08 inches. A corrective force generation device is receivable in the channel so that corrective forces generated by the corrective force generation device are transmittable to the orthodontic bracket by the pin. The channel defined by the channel defining member may be closed so as to restrict movement of the corrective force generation device within the channel in gingival, occlusal, labial, and/or lingual directions and any combination thereof.

According to another aspect of the present invention, a combinative arrangement is provided wherein the orthodontic bracket is an Edgewise orthodontic bracket having a vertically extending slot. The channel defining member is interconnected with a gingival end of the pin and the pin is insertable in an occlusal direction in the vertically extending slot of the Edgewise orthodontic bracket.

According to a further aspect of the present invention, the pin and the slot in which it is insertable are correspondingly configured to restrict rotational movement therebetween. More particularly, all or at least a portion of the pin that is insertable in the slot may have a polygonal (e.g. rectangular) cross-section and all or at least a portion of the slot in which the pin is received may have a corresponding polygonal (e.g. rectangular) cross-section. Similarly, the channel and the corrective force generation device may be correspondingly configured to restrict rotational movement therebetween. More particularly, all or at least a portion of the channel may have a polygonal (e.g. rectangular) cross-section and at least a portion of the corrective force generation device receivable therein may also have a corresponding polygonal (e.g. rectangular) cross-section. Restriction of rotational movement between the pin and the bracket, as well as between the channel and the corrective force generation device, facilitates the transmission of rotational corrective forces about mesial-distal and gingival-occlusal axes to the bracket.

According to yet another aspect of the present invention, the pin is selectively insertable in and removable from the slot of the bracket which receives the pin. This feature allows the device to be removed from the bracket when corrective forces generated by a corrective force generation device need not be applied, thereby achieving the benefits of a smaller profile bracket as compared with brackets having integrated channels for receiving corrective force generation devices. In a related aspect, the pin is bendable at a bottom end to secure the pin in the slot of a bracket. The pin may be straightened, or the bent portion may be cut-off, to remove the pin from the slot in which it is inserted.

According to a still further aspect of the present invention, the channel defining member is interconnected with the pin by an intermediate member. The intermediate member may extend laterally relative to the peripheral outer pin surface in a mesial and/or distal direction, and it may be configured for contacting a portion of the bracket. For example, the intermediate member may contact tie wings of the bracket (e.g. an Edgewise bracket) on gingival and lingual sides of the tie wings, providing additional stability when rotational forces about gingival-occlusal, mesial-distal and labial-lingual oriented axes are applied by the corrective force generation device to the channel defining member.

According to an additional aspect of the present invention, a method of applying corrective forces to a tooth involves attaching an orthodontic bracket having a vertically extending slot to the tooth. A pin of an orthodontic accessory device having a channel defining member interconnected with the pin at one end thereof is inserted into the vertically extending slot of the bracket. The channel defining member may be at a gingival end of the pin and the pin may be inserted by advancing it from a gingival position towards an occlusal opening of the vertically extending slot. A corrective force generation device is engaged in a channel defined by the channel defining member thereby making corrective forces applied by the corrective force generation device to the channel defining member transmittable to the bracket by the pin. The method may further involve bending a portion of the pin after it is inserted in the vertically extending slot to secure the device to the bracket. The method may also involve disengaging the corrective force generation device from the channel and removing the pin from the vertically extending slot thereby removing the device from the bracket.

These and other aspects and related advantages of the present invention should become apparent from a review of the following detailed description when taken in conjunction with the accompanying figures.

DETAILED DESCRIPTION

One embodiment of the orthodontic accessory device 10 of the present invention is illustrated in FIGS. 1A–B and 2A–C. The accessory device 10 includes an interconnected pin member 12 and channel defining member 14. An intermediate member 16 interconnects the channel defining member 14 with the pin 12 at one end of the pin 12. As will be appreciated, the pin member 12, channel defining member 14 and intermediate member 16 may be integrally formed.

Figure 6A:
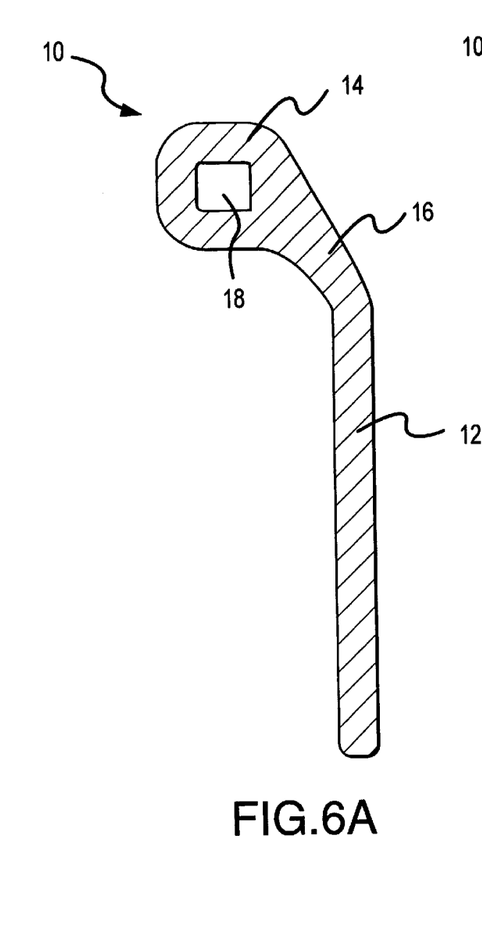
FIGS. 6A–C illustrate mesial-distal views showing orthodontic accessory devices in accordance with the present invention having alternatively configured intermediate members.
Figure 6B:
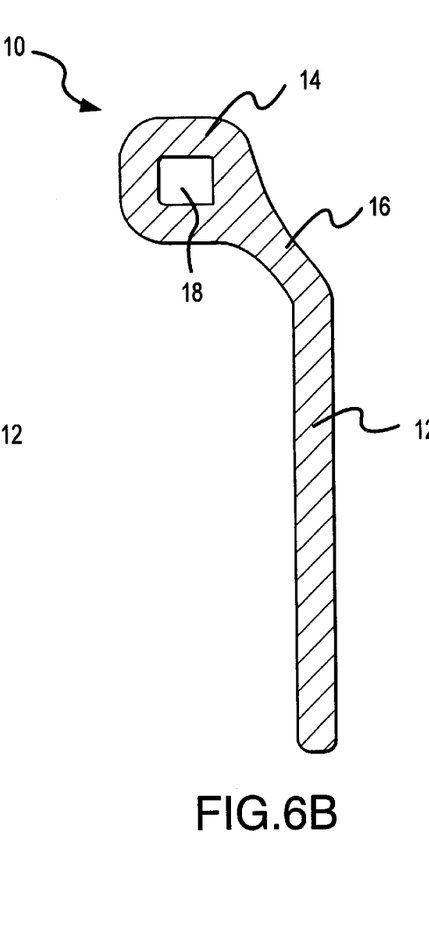
Figure 6C:
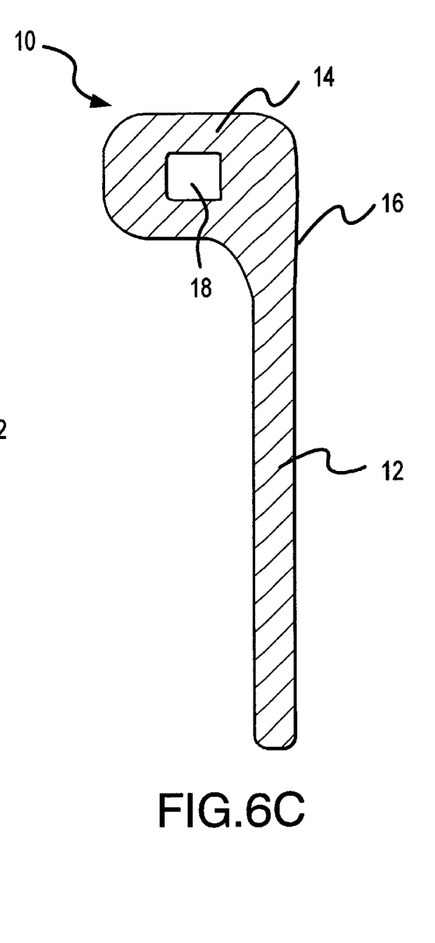

In the illustrated embodiment, the channel defining member 14 defines a closed channel 18. As shown FIG. 2A, the channel defining member 14 and the closed channel 18 defined thereby extend laterally in both a mesial and a distal direction by respective distances M, N measured relative to opposing peripheral edges of the pin 12. Similarly, the intermediate member 16 may also extend laterally in both a mesial and a distal direction by respective distances O, P measured relative to opposing peripheral edges of the pin 12. The distances O, P need not be the same as the distances M, N. Preferably, the distances of lateral extent M, N, and O, P are each at least about 0.02 inches. More preferably, distances M, N, and O, P are each between about 0.04 inches and 0.08 inches. Most preferably, distances M, N, O, and P are each about 0.05 inches. As illustrated, the intermediate member 16 is arcuately shaped so that the center axis A—A of the closed channel 18 is offset a predetermined distance from the center axis B—B of the pin 12. For example, the accurate portion of intermediate member 16 may have an inside radius of about 0.02 inches, and most preferably between about 0.01 inches and 0.03 inches. As will be appreciated, the intermediate member 16 may have other configurations as well. By way of example, the intermediate member 16 may be configured as depicted in FIGS. 6A–C. Configurations such as those depicted in FIGS. 6A–C may be most appropriate if the device 10 is to be fabricated using an injection molding/sintering process or an investment casting process.

Figure 3A:
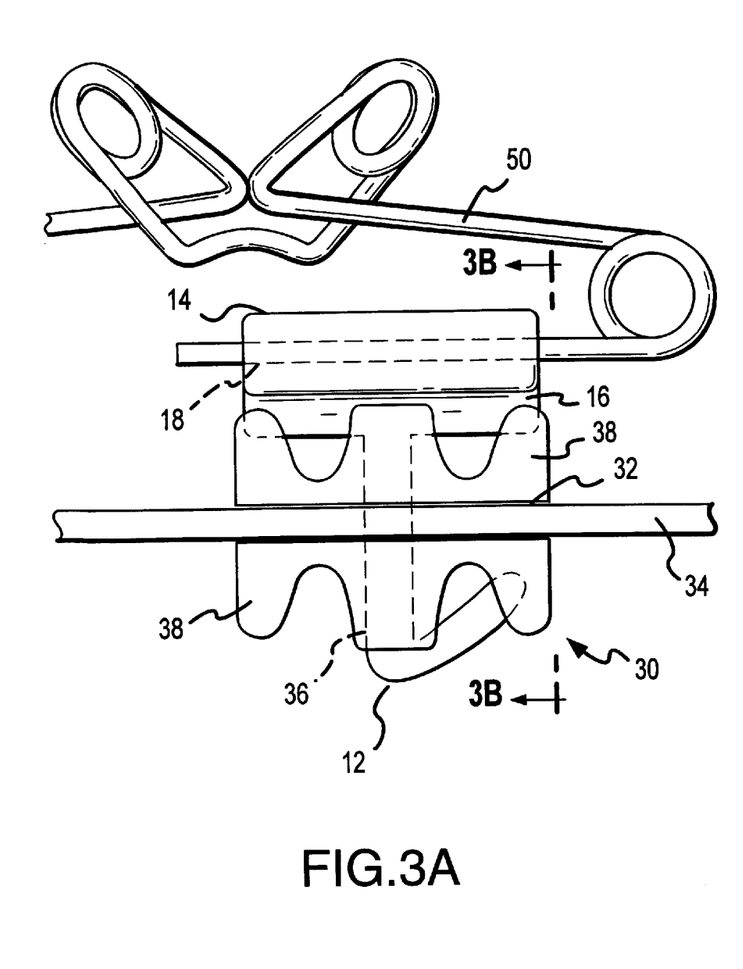
FIGS. 3A–B illustrate labial and mesial-distal views of the embodiment of FIGS. 1A–B employed with an exemplary orthodontic bracket and an exemplary corrective force generation device.
Figure 3B:
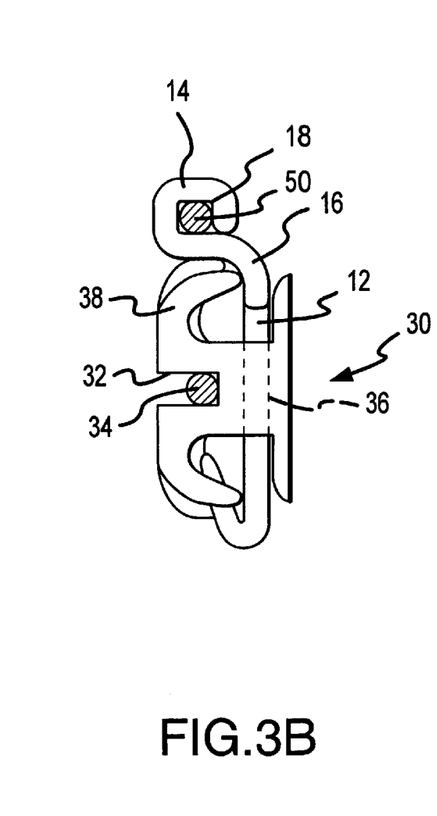

FIGS. 3A–B show the orthodontic accessory device 10 of the present invention in use with an exemplary orthodontic bracket 30 and an exemplary corrective force generation device 50. In this case, the orthodontic bracket 30 is an Edgewise bracket having a labially opening, horizontally extending slot 32 for receiving an arch wire 34 therethrough. The bracket 30 also includes a vertically extending slot 36 and two pairs of opposing tie-wings 38. The corrective force generation device 50 is of a type disclosed in U.S. Pat. No. 4,975,052 to Spencer et al. While the orthodontic accessory device 10 is particularly apt for combinative use with Edgewise brackets, those skilled in the art will appreciate that the accessory device 10 may be used with other bracket types having slots adapted for receiving a pin-shaped accessory. Further, while FIGS. 3A–B illustrate a particular type of corrective force generation device 50, the present invention may be employed with other corrective force generation devices receivable in the closed channel 18.

Figure 1A:
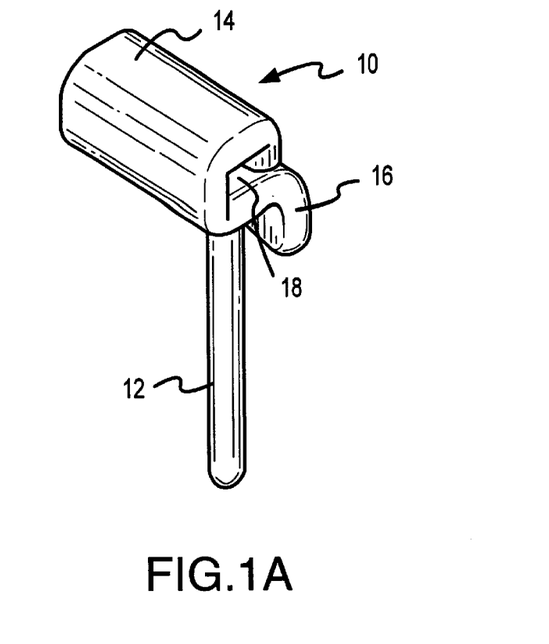
FIGS. 1A–B illustrate perspective views of one embodiment of an orthodontic accessory device in accordance with the present invention.
Figure 1B:
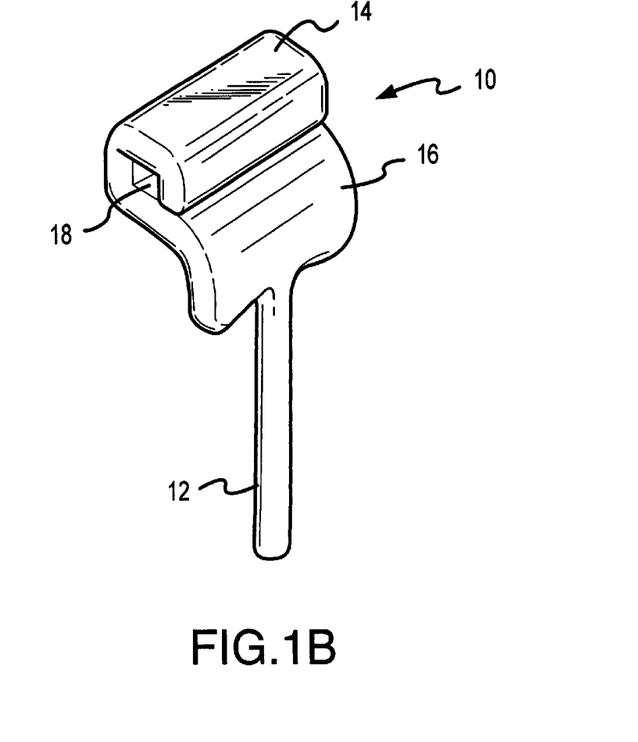
Figure 2A:
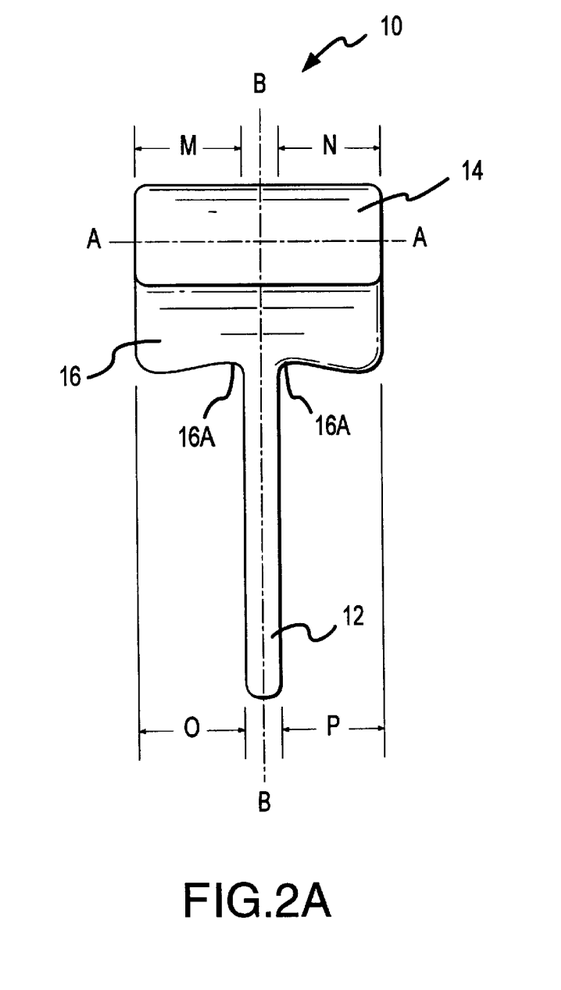
FIGS. 2A–C illustrate labial, mesial-distal and gingival views of the embodiment of FIGS. 1A–B.
Figure 2B:
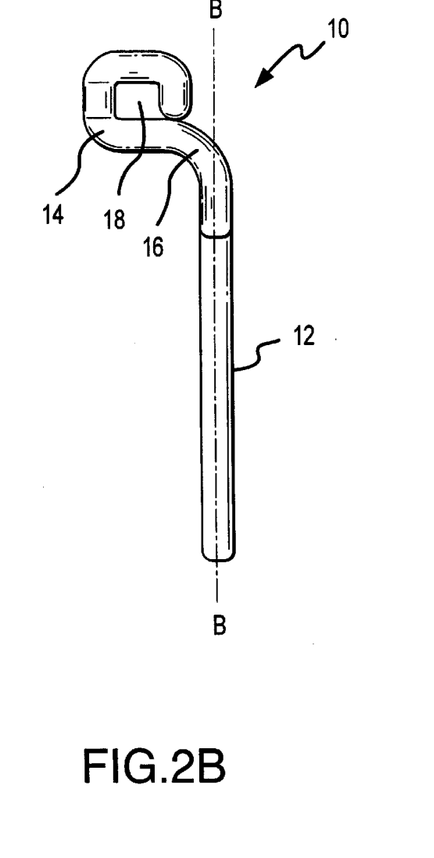
Figure 2C:
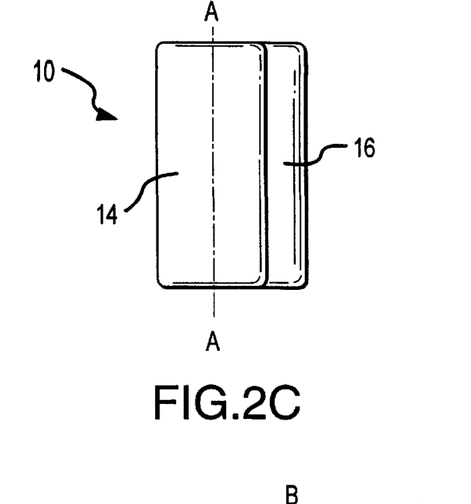

In the application of FIGS. 3A–C, the pin 12 of the orthodontic accessory device 10 is insertable through the vertical slot 36 of the bracket 30 to engage the orthodontic accessory device 10 on the bracket 30. The pin 12 is oriented so that the channel defining member 14 is located at a gingival end of the pin 12 and the pin 12 extends through the vertical slot 36 toward the occlusal surface of the tooth (when it is a bicuspid or molar) or the incisal edge of the tooth (when it is an anterior tooth). Because the gingival opening of the vertical slot 36 may have sharp corners, small indentations (e.g. tapered portions) 16A (as seen in FIG. 2A) may be formed along the edge of the intermediate member 16 where it meets the pin 12 to reduce the likelihood of binding between the device 10 and the bracket 30, thereby lessening the chance of a stress concentration during use. After insertion, an occlusal end portion of the pin 12 is bent laterally to secure the orthodontic accessory device 10 relative to the bracket 30. If the device 10 is fabricated from a metal, such as stainless steel, the pin 12 may be selectively annealed (i.e the occlusal end portion only) to soften the pin and thereby facilitate its bending. The channel defining member 14 may remain in a generally work-hardened condition to strengthen the device 10 in the area of the channel 18. Because the vertical slot 36 of the bracket 30 does not intersect the arch wire slot 32 of the bracket 30, the pin 12 is insertable in/removable from the vertical slot 36 without the need for removing the arch wire 34 from the horizontal slot 32.

As shown, the closed channel 18 of the accessory device 10 is sized to readily receive a portion of the corrective force generation device 50 inserted therethrough. The closed channel 18 may be provided to restrict movement of the corrective force generation device 50 in at least gingival, occlusal, labial and lingual directions, and any combination thereof. When the pin 12 is inserted in the vertical slot 36 and the corrective force generation device 50 is received in the closed channel 18, corrective forces applied to the channel defining member 14 by the corrective force generation device are transmittable to the bracket 30 by the pin 12 and thereby to the tooth and supporting bone.

Of note, the pin 12 of the orthodontic accessory device 10 and the vertical slot 36 of the bracket 30 may be correspondingly configured to restrict rotational movement therebetween. For example, the pin 12 may have a generally rectangularly shaped cross-section that mates with a generally rectangularly shaped vertical slot 36. By restricting rotational movement between the pin 12 and the vertical slot 36 via the noted mating engagement, rotational forces about a gingival-occlusal oriented axis applied to the channel defining member 14 of the orthodontic accessory device 10 by the corrective force generation device 50 are transmittable to the bracket 30 by the pin 12 along an extended portion of the length of slot 36 to thereby apply an enhanced corrective torque to the tooth.

The closed channel 18 and the corrective force generation device 50 may also be correspondingly configured to restrict rotational movement therebetween. As shown, the closed channel 18 may have a generally rectangular shaped cross-section for matingly receiving a portion of the corrective force generation device 50 having a corresponding, rectangular shaped cross-section. Such cooperative shaping allows rotational forces applied about a mesial-distal oriented axis to the channel defining member 14 of the orthodontic accessory device 10 (i.e., by the corrective force generation device 50) to be effectively transmitted to the bracket 30 by the pin 12.

As noted above, the intermediate member 16 extends laterally in both a mesial and a distal direction relative to opposing peripheral edges of the pin 12. Though not necessary to the basic function of the orthodontic accessory device, each extended portion of the intermediate member 16 may be configured to contact a separate one of the tie wings 38 of the bracket 30. By contacting the tie wings 38 of the bracket 30 on a lingual side thereof, the intermediate member 16 provides additional stability when rotational forces about a gingival-occlusal oriented axis are applied to the channel defining member 14 by the corrective force generation device 50. Likewise, by contacting the tie wings 38 of the bracket 30 on a gingival side thereof, the intermediate member 16 provides additional stability when rotational forces about mesial-distal and/or labial-lingual oriented axes are applied to the channel defining member 14 by the corrective force generation device 50. In a similar fashion, the channel defining member 14 may be configured so that an occlusal side of the channel defining member 14 contacts gingival sides of the tie wings 38 to also provide additional stability when rotational forces about mesial-distal and/or labial/lingual axes are applied.

Figure 4A:
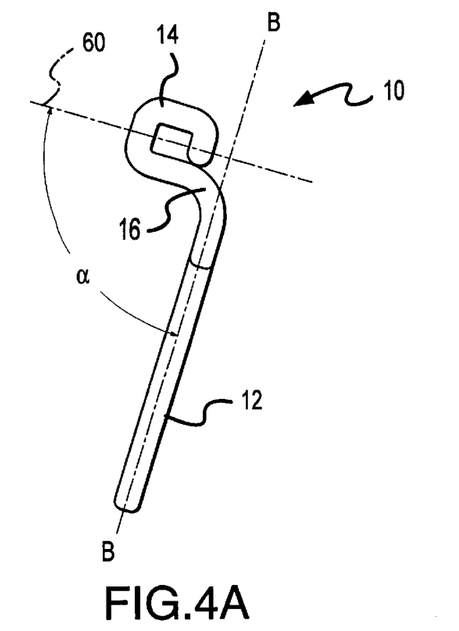
FIGS. 4A–B illustrate mesial-distal views comparing the embodiment of FIGS. 1A–B with an orthodontic accessory device in accordance with the present invention configured to enhance application of torquing forces.
Figure 4B:
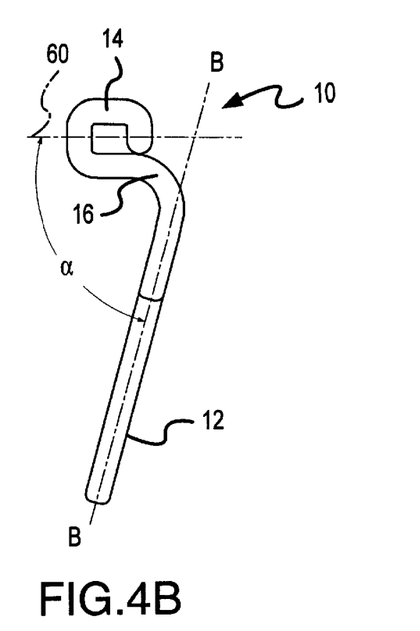

As is shown in FIGS. 4A–B and 5A–B, the device 10 of the present invention may be further configured for even more efficient application of torquing and angulating forces to a bracket 30 securable on a tooth and to accommodate and interfit with popular, commercially available fully preprogrammed brackets as well. As is shown in FIGS. 4A–B, the center axis B—B of the pin 12 of the device 10 is oriented at a first angle $\alpha$ with respect to a first plane 60 intersecting and perpendicular to labial and lingual sides of the channel defining member 14. By way of example, first angle $\alpha$ may be about 90 degrees as is shown in FIG. 4A so that the center axis B—B of the pin 12 is substantially perpendicular to the first plane 60. To improve the device 10 for transmitting torquing forces, first angle $\alpha$ is preferably between about 60 degrees and 90 degrees, and, more preferably, first angle $\alpha$ is between about 76 degrees and 82 degrees, as shown in FIG. 4B.

Figure 5A:
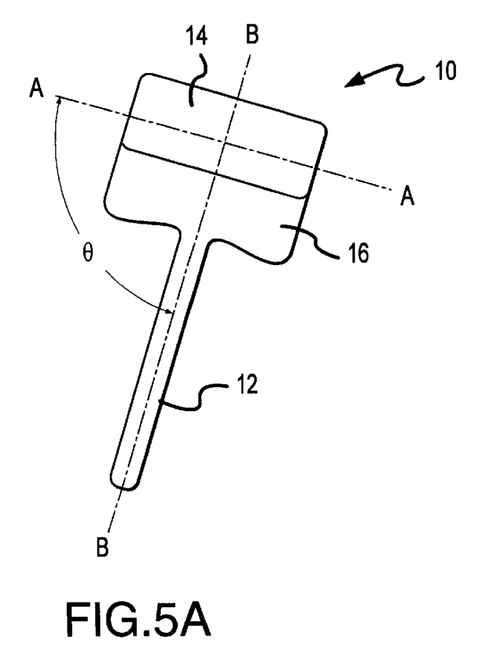
FIGS. 5A–B illustrate labial views comparing the embodiment of FIGS. 1A–B with an orthodontic accessory device in accordance with the present invention configured to enhance application of angulating forces.
Figure 5B:
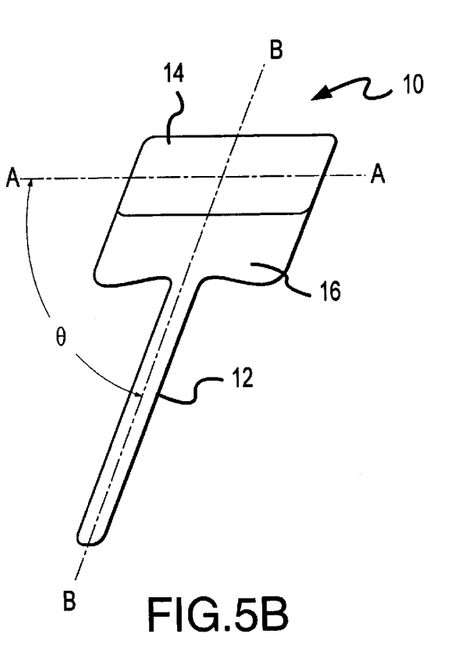

As is shown in FIGS. 5A–B, the center axis B—B of the pin 12 is oriented at a second angle $\theta$ with respect to the central axis A—A of the channel 18. By way of example, second angle $\theta$ may be about 90 degrees so that the center axis B—B of the pin 12 is substantially perpendicular to the central axis A—A of the channel 18, as shown in FIG. 5A. To improve the device 10 for transmitting angulating forces, second angle $\theta$ is preferably between about 69 degrees and 111 degrees, and, more preferably, is between about 76 degrees 104 degrees, as shown in FIG. 5B.

An orthodontic practitioner may employ the orthodontic accessory device 10 of the present invention to apply corrective forces to a patient's tooth in the following manner. A suitable bracket, such as the bracket 30 depicted in FIGS. 3A–B is attached to a patient's tooth. The pin 12 of the orthodontic accessory device 10 is then inserted through the vertical slot 36 of the bracket 30 by advancing the pin from a gingival end of the vertical slot 36 towards an occlusal end of the vertical slot 36 until the intermediate member 14 contacts the gingival surface of the body of the bracket 30 so that a portion of the pin 12 extends from the occlusal end of the vertical slot 36. This portion of the pin 12 is then bent laterally behind one of the tie wings 38 to secure the orthodontic accessory device 10 on the bracket 30. An appropriate corrective force generation device, such as the corrective force generation device 50 depicted in FIGS. 3A–B, is then engaged in the closed channel 18 so that corrective forces applied to the channel defining member 14 by the corrective force generation device 50 are transmitted to the bracket 30, and hence to the tooth, by the pin 12.

The practitioner may remove the orthodontic accessory device 10 during periods of the treatment regimen when the corrective force generation device 50 is not utilized by straightening the bent portion of the pin 12, or cutting the bent portion off, and then removing the pin 12 from the vertical slot 36. The removable nature of the orthodontic accessory device 10 provides distinct advantages as compared with orthodontic brackets having an integrated horizontal auxiliary tube for receiving a corrective force generation device. Brackets incorporating integrated horizontal auxiliary tubes typically have more bulk and a larger profile than brackets suitable for use with the orthodontic accessory device 10 of the present invention and this additional size can lead to greater irritation of the soft tissues in the patient's mouth. By removing the orthodontic accessory device 10 when not needed, the advantages of a smaller profile bracket are achieved without undertaking the considerable effort of removing the larger bracket incorporating the integrated horizontal auxiliary tube and replacing it with a smaller profile bracket.

The foregoing description of the present invention has been provided for purposes of illustration and description. This description is not intended to limit the invention and various modalities thereof. Variations, embodiments and modifications may be apparent to those skilled in the art and are intended to be within the scope of the following claims.

What is claimed is:

1. An orthodontic assembly comprising:
   an orthodontic bracket securable on a tooth, the orthodontic bracket having a main arch wire slot for receiving a main arch wire therethrough and a pin receiving slot;
   a corrective force generation device for transmitting corrective forces to said orthodontic bracket, wherein said corrective force generation device is adapted to be separate from a main arch wire; and
   an orthodontic accessory device comprising:
      a pin insertable in the pin receiving slot of the orthodontic bracket; and
      a channel defining member interconnected to said pin at one end thereof, said channel defining member defining a closed channel for receiving the corrective force generation device therethrough, and said channel extending laterally and outwardly away from a peripheral outer surface of said pin in at least one of a mesial and a distal direction;
      wherein, upon insertion of said pin into the pin receiving slot of the orthodontic bracket, said channel is maintained in separate and displaced relation to said main arch wire and said main arch wire slot of said orthodontic bracket, and corrective forces applied to said channel defining member by the corrective force generation device received in said channel are transmittable to the bracket by said pin.

2. The orthodontic accessory device of claim 1 wherein said pin is insertable in the pin receiving slot without displacing an arch wire received in the arch wire slot.

3. The orthodontic accessory device of claim 1 wherein said closed channel is oriented for receiving the corrective force generation device in a mesial-distal direction therethrough.

4. The orthodontic accessory device of claim 1 wherein said pin is adapted for selective insertion in and extraction from the pin receiving slot of the orthodontic bracket.

5. The orthodontic accessory device of claim 1 wherein the pin receiving slot and said pin are correspondingly configured to restrict rotational movement therebetween.

6. The orthodontic accessory device of claim 5 wherein at least a portion of said pin has a rectangularly shaped cross-section for receipt in a pin receiving slot of an orthodontic bracket having at least a portion that includes a corresponding rectangular cross-section.

7. The orthodontic accessory device of claim 1 wherein said pin is bendable to secure said orthodontic accessory device to the orthodontic bracket.

8. The orthodontic accessory device of claim 7 wherein said device is fabricated from a metallic material, said pin is selectively annealed to soften at least a portion of said pin thereby facilitating bending of the pin, and said channel defining member is in a generally work-hardened condition.

9. The orthodontic accessory device of claim 1 wherein said closed channel and the corrective force generation device are correspondingly configured to restrict rotational movement therebetween.

10. The orthodontic accessory device of claim 9 wherein at least a portion of said closed channel has a rectangular shaped cross-section for receiving a corrective force generation device having at least a portion that includes a corresponding rectangular shaped cross-section.

11. The orthodontic accessory device of claim 1 further comprising:
    an intermediate member interconnecting said pin and said channel defining member for contacting at least a portion of the orthodontic bracket.

12. The orthodontic accessory device of claim 11 wherein said intermediate member extends laterally relative to said peripheral outer surface of said pin in at least one of a mesial and a distal direction.

13. The orthodontic accessory device of claim 12 wherein said intermediate member and said channel extend laterally for a distance measured relative to said peripheral outer surface of said pin of at least 0.02 inches.

14. The orthodontic accessory device of claim 12 wherein said intermediate member and said channel extend laterally for a distance measured relative to said peripheral outer surface of said pin of between 0.04 inches and 0.08 inches.

15. The orthodontic accessory device of claim 12 wherein said intermediate member includes at least one arcuate indentation formed in an occlusal edge thereof and adjacent to said pin.

16. The orthodontic accessory device of claim 1 wherein said channel defining member includes labial and lingual sides and said pin is oriented at a first angle with respect to a first plane intersecting and perpendicular to said labial and lingual sides of said channel defining member.

17. The orthodontic accessory device of claim 16 wherein said first angle is between 60 degrees and 90 degrees.

18. The orthodontic accessory device of claim 16 wherein said first angle is between 76 degrees and 82 degrees.

19. The orthodontic accessory device of claim 1 wherein said pin is oriented at a second angle with respect to a central axis extending in a mesial-distal direction through said channel.

20. The orthodontic accessory device of claim 19 wherein said second angle is between 69 degrees and 111 degrees.

21. The orthodontic accessory device of claim 19 wherein said second angle is between 76 degrees and 104 degrees.

22. The orthodontic accessory device of claim 1, wherein said orthodontic accessory device is provided so that said channel defining member is positionable in a stationary location relative and adjacent to a peripheral edge of said orthodontic bracket.

23. The orthodontic accessory device of claim 22, wherein said stationary location is gingivally located relative to said peripheral edge of the orthodontic bracket.

24. An orthodontic assembly comprising:
    an Edgewise orthodontic bracket securable on a tooth, the Edgewise orthodontic bracket having a vertically extending slot and a main arch wire slot for receiving a main arch wire;

a corrective force generation device for transmitting corrective forces to said bracket, wherein said corrective force generation device is adapted to be separate from a main arch wire; and an orthodontic accessory device comprising:
  a pin slidable insertable in an occlusal direction in the vertically extending slot of the Edgewise orthodontic bracket; and
  a channel defining member interconnected to said pin at a gingival end thereof, said channel defining member defining a channel for receiving the corrective force generation device, said channel extending laterally and outwardly away from a peripheral outer surface of said pin in at least one of a mesial and a distal direction;
  wherein, upon insertion of said pin into vertically extending slot of the edgewise orthodontic bracket, said channel is maintained in separate and displaced relation to said main arch wire and said main arch wire slot of said edgewise orthodontic bracket, and corrective forces applied to said channel defining member by the corrective force generation device received in said channel are transmittable to the Edgewise orthodontic bracket by said pin.

25. The orthodontic accessory device of claim 24 wherein said channel is closed so as to restrict lateral movement of the corrective force generation device received therein.

26. The orthodontic accessory device of claim 24 wherein the Edgewise orthodontic bracket further includes a horizontally extending slot for receiving an arch wire and said pin is insertable in the vertically extending slot without displacing an arch wire received in the horizontally extending slot.

27. The orthodontic accessory device of claim 24 wherein said pin is adapted for selective insertion in and extraction from the vertically extending slot of the Edgewise orthodontic bracket.

28. The orthodontic accessory device of claim 24 wherein the vertically extending slot and said pin are correspondingly configured to restrict rotational movement therebetween.

29. The orthodontic accessory device of claim 28 wherein at least a portion of said pin has a rectangularly shaped cross-section for receipt in a vertically extending slot of an Edgewise orthodontic bracket having at least a portion that includes a corresponding rectangular cross-section.

30. The orthodontic accessory device of claim 24 further comprising:
  an intermediate member interconnecting said pin and said channel defining member for contacting at least a portion of the Edgewise orthodontic bracket.

31. The orthodontic accessory device of claim 30 wherein said intermediate member extends laterally relative to said peripheral outer surface of said pin in at least one of a mesial and a distal direction for a distance measured relative to said outer surface of said pin of between 0.02 inches and 0.08 inches.

32. The orthodontic accessory device of claim 24 wherein said channel defining member includes labial and lingual sides and said pin is oriented at a first angle with respect to a first plane intersecting and perpendicular to said labial and lingual sides of said channel defining member said first angle being between 60 degrees and 90 degrees.

33. The orthodontic accessory device of claim 24 wherein said pin is oriented at a second angle with respect to a central axis extending in a mesial-distal direction through said channel, said second angle being between 69 degrees and 111 degrees.

34. A method of applying corrective forces to a patient's tooth comprising:
  attaching to the tooth an orthodontic bracket having a vertically extending slot and a main arch wire slot for receiving a main arch wire;
  slidably inserting a pin of an orthodontic accessory device into the vertically extending slot, the orthodontic accessory device including a channel defining member interconnected with the pin and defining a closed channel extending laterally and outwardly away from a peripheral outer surface of said pin in at least one of a mesial and a distal direction for receiving a corrective force generation device, and wherein the channel is maintained in separate and displaced relation to said main arch wire and said main arch wire slot of said orthodontic bracket; and
  engaging a corrective force generation device in the closed channel, wherein said corrective force generation device is separate from said main arch wire interconnecting a main arch wire to said orthodontic bracket, and wherein corrective forces applied to the channel defining member by the corrective force generation device received in the closed channel are transmittable to the bracket by the pin.

35. The method of claim 34 wherein in said step of inserting the pin, the pin is inserted by advancing it from a gingival towards an occlusal opening of the vertically extending slot and the channel defining member is at a gingival end of the pin.

36. The method of claim 34 further comprising the step of:
  bending a portion of the pin, after inserting the pin in the vertically extending slot, to secure the orthodontic accessory device to the orthodontic bracket.

37. The method of claim 34 further comprising, after the corrective forces are applied to the tooth for a period of time, the steps of:
  disengaging the corrective force generation device from the channel; and
  extracting the pin from the vertically auxiliary slot of the orthodontic bracket.

38. The method of claim 34 further comprising the step of:
  maintaining said channel defining member in a stationary location relative and adjacent to a peripheral edge of the orthodontic bracket.

39. The method of claim 30, said maintaining step including:
  bending a portion of the pin, after inserting the pin in the vertically extending slot, to secure the orthodontic accessory device to the orthodontic bracket.

40. The method of claim 38, wherein said stationary location is gingivally disposed relative to said to peripheral edge of tile orthodontic bracket.

41. A method of applying corrective forces to a patient's tooth having an orthodontic bracket secured thereon, said method comprising:
  applying the corrective forces by a corrective force generation device to a channel defining member of an orthodontic accessory device, wherein said channel defining member is selectively positioned in a stationary location relative and adjacent to a peripheral edge of the orthodontic bracket, wherein the corrective forces act on a first point of action remote from the orthodontic bracket, and wherein the corrective generation device is separate from a main arch wire engageable with a main arch wire slot of the bracket; and translating the corrective forces acting on the first point of action to the orthodontic bracket via an elongated pin of the orthodontic accessory device slidably inserted into a pin receiving slot of the orthodontic bracket, wherein the channel defining member extends literally away from the pin, and wherein the corrective forces are translated by the orthodontic bracket to the tooth and;

wherein the first point of action is located relative to the orthodontic bracket such that the effective point of action of the corrective forces on the tooth is closer to the center of resistance to movement of the tooth than if the corrective forces were applied directly to the orthodontic bracket.

42. The method of claim 41 wherein the first point of action is located in a gingival direction from a central point of the orthodontic bracket.

* * * * *

UNITED STATES PATENT AND TRADEMARK OFFICE
CERTIFICATE OF CORRECTION

PATENT NO. : 5,993,207
DATED : November 30, 1999
INVENTOR(S) : SPENCER, William A.

It is certified that error appears in the above-identified patent and that said Letters Patent is hereby corrected as shown below:

Claim 40, Column 10, line 53, delete "tile" and insert --the--.
Claim 41, Column 11, line 5, delete "literally" and insert --laterally--.

Signed and Sealed this

Eleventh Day of July, 2000

Attest:

Q. TODD DICKINSON

*Attesting Officer*      *Director of Patents and Trademarks*